United States Patent [19]

Howlett

[11] Patent Number: 4,896,832

[45] Date of Patent: Jan. 30, 1990

[54] DISPENSING APPARATUS FOR METERED QUANTITIES OF PRESSURISED FLUID

[75] Inventor: David J. Howlett, Grimston, United Kingdom

[73] Assignee: Bespak PLC, King's Lynn, United Kingdom

[21] Appl. No.: 236,397

[22] Filed: Aug. 25, 1988

[30] Foreign Application Priority Data

Sep. 9, 1987 [GB] United Kingdom ............... 8720976
Aug. 1, 1988 [GB] United Kingdom ............... 8818285

[51] Int. Cl.$^4$ ............................................. B05B 11/02
[52] U.S. Cl. ..................... 239/322; 239/323; 239/470; 239/471; 239/493; 222/95; 222/162; 222/386.5; 222/389; 222/402.2; 92/250
[58] Field of Search ............... 222/105, 162, 160, 389, 222/386.5, 402.2, 387, 402.13, 95; 92/250, 249; 184/39, 39.1; 277/DIG. 6, 165; 239/322, 323, 329, 337, 373, 470, 471, 483, 488, 489, 493

[56] References Cited

U.S. PATENT DOCUMENTS

| | | | |
|---|---|---|---|
| 2,904,223 | 9/1959 | Ryan | 222/162 |
| 3,310,830 | 3/1967 | Gattone | 222/162 |
| 3,456,646 | 7/1969 | Phillips et al. | 128/200.23 |
| 3,652,018 | 3/1972 | Focht . | |
| 4,045,860 | 9/1977 | Winckler . | |
| 4,433,797 | 2/1984 | Galia | 222/402.2 |
| 4,685,597 | 8/1987 | Hirao et al. | 222/389 |
| 4,801,093 | 1/1989 | Brunet et al. . | |

FOREIGN PATENT DOCUMENTS

| | | | |
|---|---|---|---|
| 0030990 | 7/1981 | European Pat. Off. . | |
| 48501 | 1/1985 | European Pat. Off. | 128/200.23 |
| 1491714 | 5/1969 | Fed. Rep. of Germany | 128/200.23 |
| 1379197 | 10/1964 | France . | |
| 2040183 | 1/1971 | France . | |
| 2554792 | 5/1985 | France . | |
| 872187 | 7/1961 | United Kingdom . | |
| 1120945 | 7/1968 | United Kingdom . | |
| 2015655 | 9/1979 | United Kingdom | 222/389 |
| 2050303 | 1/1981 | United Kingdom . | |

Primary Examiner—H. Grant Skaggs
Attorney, Agent, or Firm—Beveridge, DeGrandi & Weilacher

[57] ABSTRACT

A dispensing apparatus comprises a pressurised dispensing container (3), a housing (2) for the container defining a bore, the container having a body (50) which is axially slidable in the bore, the container having a collapsible metering valve (8) located at a first end (6) of the body for dispensing metered quantities of fluid and actuated by axial depression of a valve stem (9) defining a dispensing flowpath, a valve actuator (11) fixedly connected to the housing at a corresponding first end (7) thereof and defining a further dispensing flowpath for product fluid dispensed through the stem, and trigger means (30) operable to urge the container body axially towards the first end of the housing such that the valve stem is depressed by relative movement together of the valve and actuator and thereby dispensing a metered quantity of fluid, wherein the container body defines a chamber (4) and the container includes means (5) dividing the chamber into a product fluid reservoir (25) communicating with the valve and a propellant fluid reservoir (26), the dividing means being movable such that propellant pressure is applied to the product fluid without mixing of the respective fluids. The apparatus is suitable for the nasal administration of insulin.

20 Claims, 5 Drawing Sheets

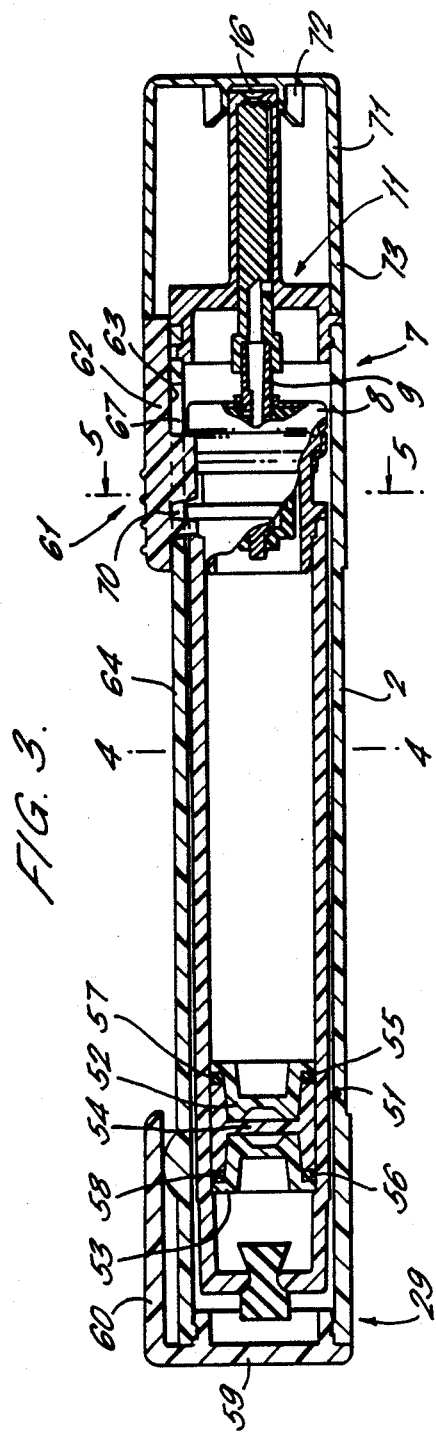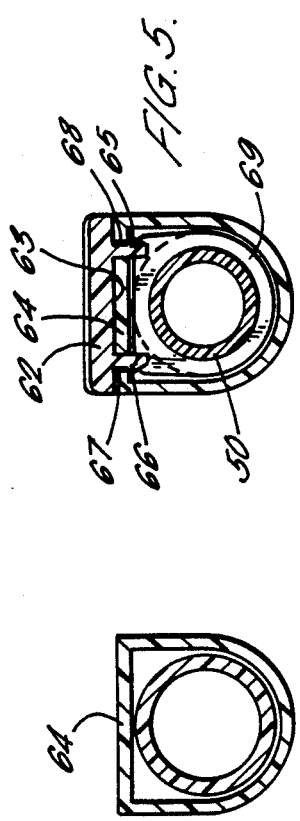

DISPENSING APPARATUS FOR METERED QUANTITIES OF PRESSURISED FLUID

This invention relates to dispensing apparatus for dispensing metered quantities of pressurised fluid and in particular but not exclusively to dispensing apparatus for the nasal administration of medicinal products such as insulin.

According to the present invention there is disclosed dispensing apparatus for dispensing metered quantities of a pressurised fluid comprising a pressurised dispensing container, a housing for the container defining a bore, the container having a body which is axially slidable in the bore, the container having a collapsible chamber metering valve located at a first end of the body for dispensing metered quantities of fluid and actuated by axial depression of a valve stem defining a dispensing flowpath, a valve actuator fixedly connected to the housing at a corresponding first end thereof and defining a further dispensing flowpath for product fluid dispensed through the stem, and trigger means operable to urge the container body axially towards the first end of the housing such that the valve stem is depressed by relative movement together of the valve and actuator and thereby dispensing a metered quantity of fluid, wherein the container body defines a chamber and the container includes means dividing the chamber into a product fluid reservoir communicating with the valve and a propellant fluid reservoir, the dividing means being movable such that propellant pressure is applied to the product fluid without mixing of the respective fluids.

An advantage of such an arrangement is that contamination by propellant of the product fluid is avoided. This is particularly important when the product fluid is a medicinal product and especially where the propellant fluid is known to have harmful effects on the person receiving medication or adverse effects on the quality of the product fluid.

A further advantage is that the collapsible chamber metering valve enables the metered dose to be substantially unaffected by the attitude at which the apparatus is held in use. The provision of trigger means also has the advantage of enabling the housing and the valve actuator to be held in a substantially fixed position in use and this is particularly convenient where the use requires precise control of the actuator position as in the case of nasal administration of a medicinal product.

The dividing means may comprise a free piston axially slidable within the chamber and dividing the chamber into a first portion constituting the product fluid reservoir located forward of the piston and a second portion constituting the propellant fluid reservoir located rearward of the piston.

In such an arrangement the piston may comprise a forward portion of a first material selected to be substantially chemically non-reactive with the product fluid and a rearward portion of a second material selected to be substantially impermeable to the propellant fluid, the piston portions being composited such that the product and propellant fluids respectively do not contact the second and first materials of the piston respectively.

The piston portions may be formed of resilient materials and each portion may include a respective seal formation resiliently biassed into peripheral sealing contact with the inner wall of the container. The respective portions may then each be formed of respective plastics materials and the respective seal formations comprise annular projections formed integrally with the respective portions.

Alternatively the first and second materials may be elastomeric, the respective seal formations comprising annular projections of part circular cross-section formed integrally with the respective portions.

The piston constituting the dividing means may alternatively comprise a substantially rigid piston body, first seal means peripherally sealing the piston body to the inner wall of the container and formed of a material selected to be substantially chemically non-reactive with the product fluid and second seal means peripherally sealing the piston to the inner wall of the container at a location rearward of the first seal means and formed of a material selected to be substantially impermeable to the propellant fluid. The piston body in this case is formed from an inert and gas impermeable material such as a rigid plastics material or a metallic material for example.

The first seal means may be a ring of bromobutyl rubber material and the second seal means may be a ring of nitrile rubber material.

Bromobutyl rubber material has been found to be particularly suited where the product fluid contains insulin because this material is less prone to contaminate the product with weak organic acids than in the case of other rubber materials of similar mechanical properties. Such acids are known to render insulin unstable.

Nitrile rubber material is particularly suited for use with hydrocarbon propellant fluids where it exhibits exceptionally low gas permeability.

The piston body may comprise a forward portion, a rearward portion spaced axially and rearwardly of the forward portion and a connecting portion co-operating with the forward and rearward portions to define first and second annular grooves receiving the first and second seal means respectively.

Such an arrangement enables the piston to be conveniently formed from easily mouldable components and facilitates assembly with the seal means.

The apparatus may alternatively include a dividing means comprising a flexible bag. The interior of the bag may define the product reservoir with the mouth of the bag comprising an annular flange secured in sealing contact with a co-operating flange of the valve.

The container may then be secured to the valve by means of a crimped valve ferrule such that the flange comprising the bag mouth is clamped between an annular lip of the container mouth and the valve flange.

The space between the external surface of the bag and the container wall thereby defines the propellant reservoir in such an arrangement.

Alternatively the propellant may be contained within the flexible bag with the product reservoir external to the bag. In this case the valve would communicate with the chamber so as to communicate with the product reservoir.

The actuator may comprise inner and outer nested components, the actuator including a break-up nozzle for atomising dispensed fluid, which nozzle includes swirl inducing ducts defined by groove formations formed in one or other abutting surfaces of the inner and outer nested components respectively.

An advantage of such an actuator is that the need for a nozzle disk is obviated and avoids the danger that such a disc might otherwise be displaced during a dispensing operation. This is particularly important where a medicinal product is dispensed for inhalation nasally or orally in which case a displaced nozzle disk would present a serious hazard.

Preferably the inner nested component includes a first tubular portion fitting onto a stem of a co-operating dispensing valve, the outer nested component including a second tubular portion fitting onto the first tubular portion and the first tubular portion being provided with an axially extending groove defining an axially extending dispensing flowpath.

The trigger means may comprise a trigger member which is pivotally mounted with respect to the housing and further comprising means transmitting pivotal movement of the trigger member to axial movement of the container.

Alternatively the trigger member may be slidable with respect to the housing and may further comprise means transmitting sliding movement of the trigger member to axial movement of the container. Such a trigger member may include at least one projection extending through an aperture of the housing and engaging a co-operating formation of the container, the trigger member being axially slidable and the container being slidable in unison therewith with respect to the housing.

Optionally the trigger means includes audible indicator means such that an audible indication is generated upon each actuation of the trigger means.

The generation of such an indication is important when a medicinal product is dispensed nasally and the patient is unable to sense the delivery of a metered dose.

Advantageously the dispensing apparatus includes viewing means for viewing the quantity of fluid remaining in the container. The viewing means in a preferred embodiment comprises a transparent window formed in the housing.

Conveniently the apparatus further includes locking means for selectively locking the trigger means against accidental actuation when not in use.

Conveniently the apparatus further includes a detachable cap for the first end of the housing, which cap includes a pocket clip means. The dispensing apparatus when so assembled with a cap may then have the external appearance of a conventional fountain pen and may be carried in the pocket of the user in like manner.

Particular embodiments of the present invention will now be disclosed by way of example only and with reference to he accompanying drawings of which;

FIG. 3 is a sectional view of an alternative apparatus including a sliding trigger member;

FIG. 4 is a section at 4—4 of the apparatus of FIG. 3;

FIG. 5 is a section at 5—5 of the apparatus of FIG. 3;

Figure 1:
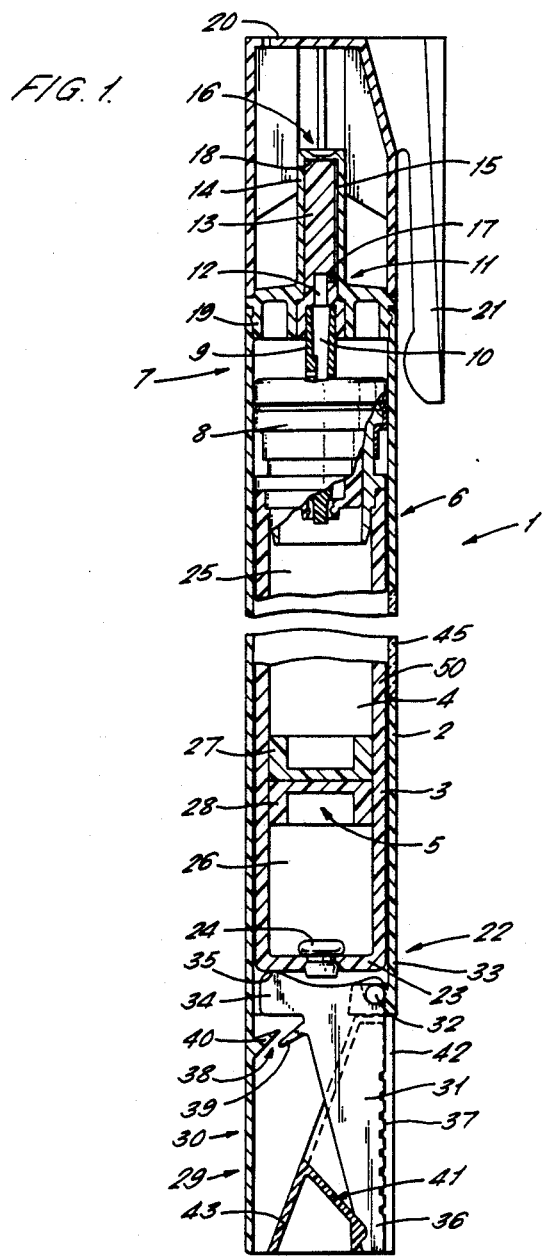
FIG. 1 is a part sectional elevation of a dispensing apparatus in accordance with the present invention and including a pressurised dispensing container in which the dividing means is a piston.

The apparatus 1 of FIG. 1 comprises a cylindrical housing 2 defining a bore within which a cylindrical pressurised dispensing container 3 is located such that a body 50 of the container is coaxially slidable. The container 3 defines a cylindrical chamber 4 within which a free piston 5 is coaxially slidable. A first end 6 of the container 3 is located at a first end 7 of the housing and includes a collapsible chamber metering valve 8 of the type which is actuated by depression of a valve stem 9 relative to the valve body. The construction of the valve 8 is such that the stem 9 is spring biassed into a normally extended position in which the valve is in a closed (non-dispensing) condition. A dispensing channel 10 extends axially through the valve stem 9 and defines a dispensing flowpath.

An actuator 11 is connected to the housing 2 at the first end 7 and receives the valve stem 9 in an axial bore 12.

The actuator 11 is of two part construction comprising an inner component 13 and an outer component 14, the components being nested together.

The inner nested component 13 is cylindrical and extends coaxially with the housing and includes an axially extending groove 15 which is overlaid by the outer nested component 14 to define a flowpath for dispensed fluid, the flowpath communicating between a nozzle 16 formed in the outer nested component and a radial port 17 communicating with the bore 12. Swirl inducing ducts 18 are provided by surface formations in mating surfaces of the inner component 13 and the outer component 14 adjacent to the nozzle 16.

The fluid flowpath provided by the actuator 11 therefore extends from the stem channel 10 into the bore 12, through the port 17 into the groove 15, through the swirl inducing ducts 18 and out through the nozzle 16.

In the drawings the swirl inducing ducts 18 are shown only as a thickening of the line defining the upper-most end of the inner nested component 13. The ducts are arranged to conduct fluid in a generally radially inwardly direction whilst inducing swirl movement in the conducted fluid, the shape of the ducts corresponding to the ducts provided in known break-up nozzle disks.

The outer nested component 14 includes an annular outer rib 19 which is a snap fit within the first end 7 of the housing 2 thereby forming an end closure to the housing. The cap 20 is a push fit onto the actuator 11 and provides a protective enclosure when the apparatus 1 is not in use. The cap 20 includes a pocket clip 21 similar to that provided on conventional fountain pens.

The container 3 has a body of a transparent plastics material which is closed at its first end 6 by the valve 8 and at its second end 22 by an end wall 23. An elastomeric plug 24 is provided in the end wall 23 to allow filling of the container with propellant.

The piston 5 within the container 3 divides the chamber 4 into a product fluid reservoir 25 forward of the piston i.e. adjacent to the first end 6 and a propellant reservoir 26 rearward of the piston i.e. adjacent to the second end 22. The piston 5 is of composite construction and formed from a forward portion 27 of butyl rubber material which is disposed facing the product fluid reservoir 25. A rearward portion 28 of the piston 5 is formed of nitrile rubber material and is disposed facing the propellant fluid reservoir 26. Each of the piston portions 27 and 28 is formed having a cylindrical cup shape and the portions are connected in back-to-back fashion such that the composite piston 5 is of H-section.

Portion 27 and rearward portion 28 are bonded together during the moulding operation by which the piston is formed.

The piston 5 is freely slidable in the axial direction along the container 3 whilst forming a sufficiently tight seal against the container walls to prevent mixing of the propellant fluid and product fluid. The composite construction of the piston 5 ensures that the propellant fluid comes into contact only with nitrile material of the piston and that the product fluid comes into contact only with the butyl material of the piston.

A second tubular end 29 of the housing projects beyond the second end 22 of the container and incorporates manually operable trigger means 30. The trigger means 30 comprises a trigger member 31 which is pivotally mounted about a pivot 32 which is located adjacent to a sidewall portion 33 of the housing with a pivotal axis being defined tangentially with respect to the sidewall portion. The trigger member 31 includes a cam 34 having a cam surface 35 arranged in contact with the end wall 23 of the container 3. The trigger member 31 further includes a lever arm 36 which extends generally axially with respect to the housing 2 and includes a finger grip surface 37. The trigger member 31 is configured such that upon depression of the lever arm 36 the trigger member rotates about the pivot 32 such that the cam 34 bears upon the end wall 23 in order to urge the container axially along the housing 2 in a direction away from the trigger means.

The trigger means 31 further comprises an audible indicator means 38 comprising a resilient detent 39 extending generally radially with respect to the pivot 32 and co-operating with a fixed detent 40 extending generally inwardly of the housing 2 such that during depression of the trigger lever arm 36 the respective detents 39 and 40 are snap engageable to produce an audible click.

Figure 2:
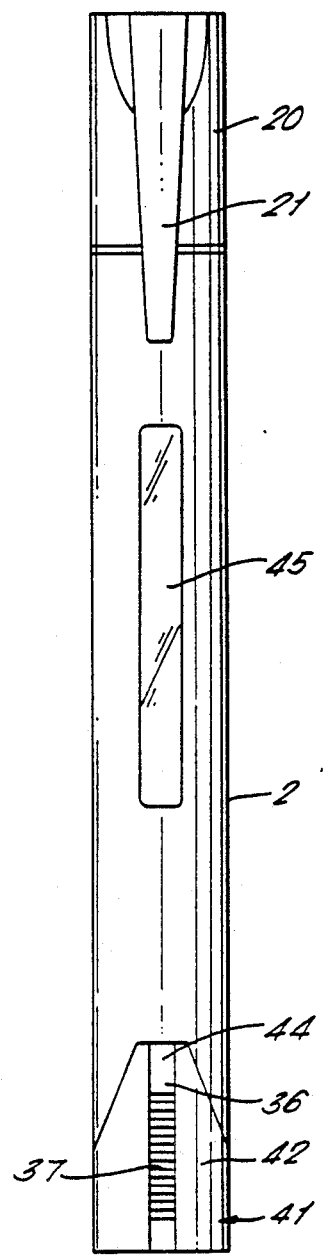
FIG. 2 is a side view of the apparatus of FIG. 1.

A locking clip 41 is provided for locking the trigger means in an inoperative condition as shown in FIGS. 1 and 2. The locking clip 41 is part cylindrical having an outer portion 42 which overlays one side of the second end 29 of the housing 2 so as to cover the lever arm 36 and includes an inner portion 43 in the form of an insert within the open second end 29 of the housing and which is configured so as to positively restrain the lever arm 36 from accidental rotation. The inner portion 43 and the lever arm 36 are snap engageable such that the locking clip 41 may be removed by moving axially away from the housing 2 before use of the apparatus 1.

As seen in FIG. 2 the locking clip 41 includes an axially extending slot 44 through which the lever arm 36 is visible.

As seen in FIG. 2 the housing 2 includes a window 45 through which the product fluid reservoir 25 may be inspected in order to determine the quantity of product fluid remaining.

In use to dispense a metered dose of the product fluid the cap 20 together with the locking clip 41 are removed from the housing 2. The apparatus 1 is then postioned with the nozzle 16 directed towards the location to which product is to be dispensed and the trigger means 30 is actuated by depression of the lever arm 36. Upon depression of the lever arm 36 the trigger member 31 pivots about the pivot 32 and the cam 34 is similarly pivotally rotated such that the second end of the container is urged away from the trigger means 30 by action of the cam surface 35.

The container body 50 is thereby moved axially along the housing 2 and the valve 8 is therefore moved towards the fixed actuator 11 such that the stem 9 is depressed. Upon sufficient depression on the stem 9 the metering valve 8 is actuated and a metered dose of product fluid is discharged through the channel 10 of the stem 9, through the port 17 into the groove 15 and is thereby conducted to the nozzle 16 via the swirl inducing ducts 18. An atomised spray of product fluid is thereby dispensed.

The lever arm 36 is then released so that the container 3 is no longer biassed into contact with the actuator 11. The valve 8 is then urged away from the actuator 11 by action of the spring-loaded stem 9 so that the container body 50 is moved back along the housing 2 thereby returning the lever arm to its original rest position.

At the same time as this return stroke is achieved the metering valve recharges its collapsible chamber by drawing product fluid from the reservoir 25, the product fluid being pressurised by action of the piston 5 which communicates to the product reservoir the pressure provided by a hydrocarbon propellant within the propellant fluid reservoir 26. As product fluid is drawn from the product reservoir 25 an imbalance of pressure is created across the piston 5 so that piston moves axially towards the first end 7 of the housing 2 until pressure is equalised.

During both actuating and return strokes of the trigger means 31 the audible indicator means 38 generates a click as described above.

An alternative apparatus shown in FIG. 3 is similar in many respects to the apparatus of FIG. 1 so that this apparatus will be described using corresponding reference numerals where appropriate. The apparatus of FIG. 3 includes an alternative piston 51 having a forward piston portion 52 which is connected to a rearward piston portion 53 by a connecting portion 54.

The connecting portion 54 is of H-section and receives the forward and rearward portions 52 and 53 as a push fit, the three portions together combining a composite body of the piston 51. The portions 52, 53 and 54 interfit so as to define first and second annular grooves 55 and 56 which accommodate first and second ring seals 57 and 58 of rectangular cross-section formed of bromobutyl rubber material and nitrile rubber material respectively. The first and second seals 57 and 58 are axially spaced with the first seal located forward of the second seal such that only the first seal contacts the contents of the product reservoir 25. The bromobutyl rubber material is selected to be substantially chemically non-reactive with a product containing insulin.

The second seal 58 is located rearward of the first seal and is selected to be impermeable to hydrocarbon propellant fluid received in the propellant reservoir 26.

The second end 29 of the housing 2 is closed by an insert 59 which is received as a snap fit within the second end and a pocket clip 60 is formed integrally with the insert.

The apparatus of FIG. 3 includes an alternative trigger means 61 located adjacent the first end 7 of the housing. The trigger means 61 includes a trigger member 62 having a flat surface 63 in sliding contact with a flat face 64 formed on the housing 7 which is of D-shaped cross-section.

The trigger member 62 includes projections 65 and 66 which extend through axially extending slots 67 and 68 formed in the housing 7, the projections being shaped so as to be received as a snap fit within the slots in order to captively retain the trigger member in sliding contact with the housing.

The container body 50 has a radially extending annular flange 69 which is of D-shape when viewed in axial projection so as to be a sliding fit within the housing 2 at a location adjacent the trigger member 62. The projections 65 and 66 are recessed to define a radially extending groove 70 receiving the flange 69 such that axial motion of the trigger member 62 imparts axial motion to the container body 50.

The apparatus of FIG. 3 includes a cap 71 having a gripping formation 72 within the cap which is arranged to be a push fit on to the actuator 11. When not in use the nozzle may therefore be sealed by fitting the cap onto the actuator.

The cap 71 includes sidewalls 73 which extend into contact with the housing 2 when the cap is fitted on to the actuator 11 and such that the sidewall abuts the trigger member 62 such that the trigger member is retained in its most rearward position as shown in FIG. 3. This arrangement resists accidental actuation by unwanted movement of the trigger member.

The cap 71 is removed from the actuator 11 by twisting movement in either direction, separation of the cap from the actuator being provided by engagement between the cap mouth and ramped surfaces of the actuator (not visible in FIG. 3).

In use to dispense a metered dose of the product fluid the cap 71 is removed from the actuator 11 and the apparatus is held in position with the nozzle 16 directed towards the location to which product is to be dispensed. The trigger means 61 is then actuated by sliding movement of the trigger member 62 in a direction towards the actuator 11, this motion being communicated to the container body 50 by action of the projections 65 and 66 engaging the flange 69.

The container body 50 is thereby moved axially along the housing 2 towards the actuator 11 such that the stem 9 is depressed. Upon sufficient depression of the stem 9 the metering valve 8 is actuated and a metered dose of the product fluid is discharged as an atomised spray of product fluid.

The trigger member 62 is then released so that the container body 50 is no longer biassed into contact with the actuator 11. The valve 8 is then urged away from the actuator 11 by action of the spring-loaded stem 9 so that the container body 50 is moved back along the housing 2 thereby returning the trigger member 62 to its original rest position as shown in FIG. 3.

Figure 7:
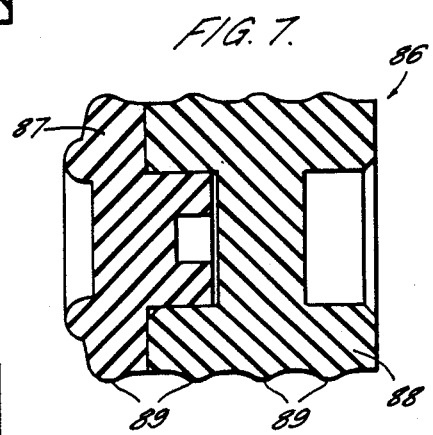
FIG. 7 is a sectional view of a further alternative piston having a forward portion of an elastomeric material and a rearward portion of a different elastomeric material.
Figure 8:
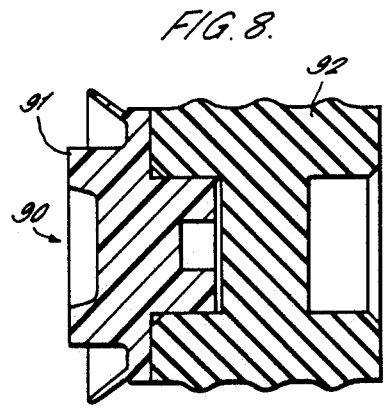
FIG. 8 is a sectional view of a further alternative piston having a forward portion of a resilient plastics material and a rearward portion of an elastomeric material.
Figure 9:
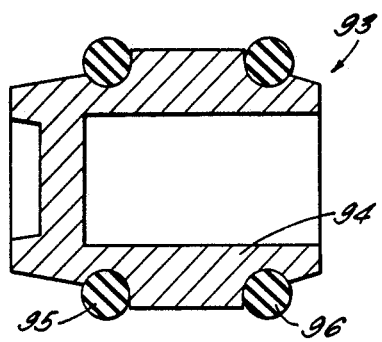
FIG. 9 is a sectional view of a further alternative piston having a rigid metal body and O-ring seal means.

Further alternative piston arrangements are shown in FIGS. 7 to 9 as described below.

Figure 6:
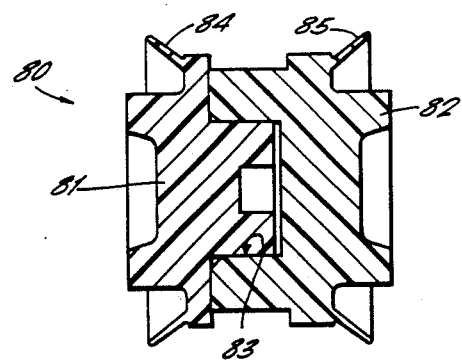
FIG. 6 is a sectional view of an alternative piston having two portions formed of resilient materials.

In FIG. 6 a piston 80 comprises a forward portion 81 and a rearward portion 82 each formed of a resilient plastics material i.e. low density polyethylene. The portions 81 and 82 are connected by means of push fit formations 83 and include respective annular projections 84 and 85 which in use extend into peripheral sealing contact with the inner wall of the container body 50. In FIG. 6 the projections 84 and 85 are shown in their relaxed state in which they extend at 45° to the longitudinal axis of the piston 80. When assembled within the chamber 4 the pistons are deflected radially inwardly so as to be resiliently biassed into sealing contact with the walls of the container body 50.

In FIG. 7 an alternative piston 86 is shown having a forward portion 87 of an elastomeric material i.e. bromobutyl and a rearward portion 88 formed of a different elastomeric material i.e. nitrile rubber. Both portions 87 and 88 include annular projections 89 in the form of ribs of part circular cross-section which in use extend into peripheral sealing contact with the walls of the container body 50.

FIG. 8 shows a further variant in which piston 90 includes a forward portion 91 corresponding to the forward portion 81 of FIG. 6 and a rearward portion 92 corresponding to the rearward portion 88 of FIG. 7. The forward and rearward portions in both FIGS. 7 and 8 are interconnected by push fit formations as in the case of the piston 80 of FIG. 6.

A further alternative piston 93 is shown in FIG. 9 in which a metal piston body 94 is circumferentially grooved to accommodate forward and rearward O-ring seals 95 and 96 respectively formed on bromobutyl rubber material and nitrile rubber material respectively.

Figure 10:
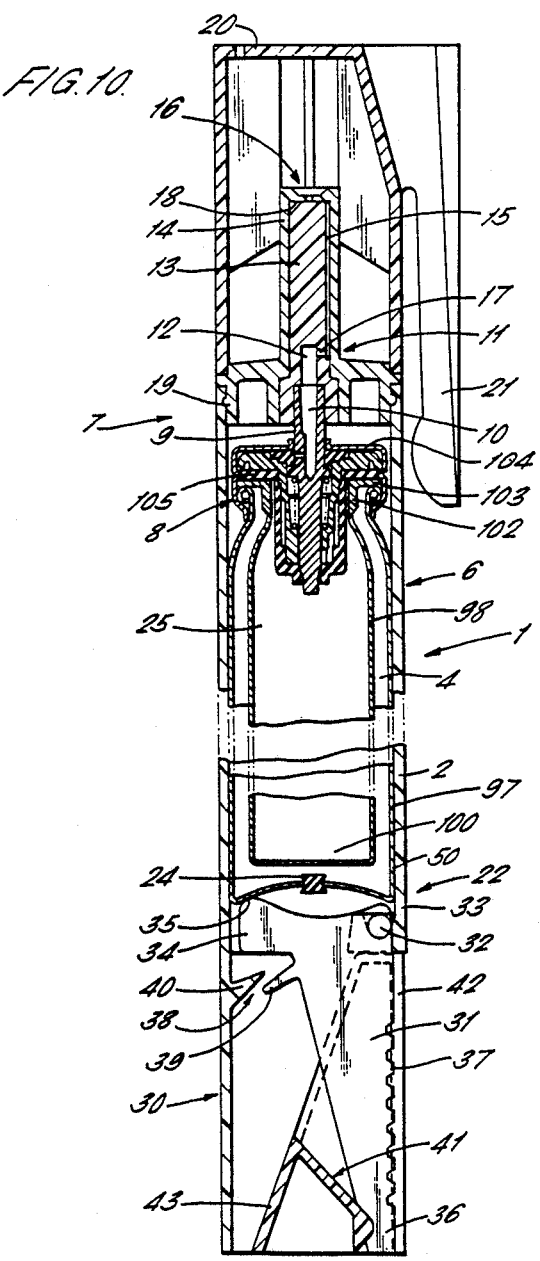
FIG. 10 is a sectional view of an alternative apparatus including a flexible bag constituting the dividing means.

A further alternative apparatus is shown in FIG. 10 in which corresponding reference numerals to those used in FIG. 1 are used where appropriate.

The apparatus of FIG. 10 comprises a cylindrical housing 2 within which a container body 50 is axially slidable in response to actuation of trigger means 30 of the type described with reference to FIG. 1. The container body 50 forms part of an alternative container 97 within which the product reservoir 25 is divided from the propellant reservoir 26 by means of a flexible bag 98.

The bag 98 has a thickened mouth portion 102 including a radially extending annular flange 103, the portion and the flange being formed integrally with the bag.

The container body 50 is secured to the valve 8 by means of a crimped valve ferrule 104 which also serves to secure the flange 103 of the mouth portion 102 in sealing contact with a co-operating flange 105 of the valve. The bag 98 and the valve 8 therefore combine to define a closed product fluid reservoir 25 from which product fluid 100 may be dispensed by operation of the valve.

The bag 98 within the container 97 thereby divides the chamber into a product fluid reservoir 25 within the bag and a propellant reservoir 26 external to the bag.

The construction of the apparatus shown in FIG. 10 other than the internal construction on the container 97 conforms to the construction of the apparatus of FIG. 1.

In use to dispense a metered dose of product fluid 100, the trigger means 30 is actuated as described above with reference to FIG. 1 so that a metered dose is dispensed by the valve 8. On release of the trigger means 30 the valve 8 is urged away from the actuator 11 by action of the spring-loaded stem 9 so that the container 97 is moved back along the housing 2 thereby returning the lever arm to its original rest position.

At the same time as this return stroke is achieved the metering valve recharges its collapsible chamber by drawing product fluid from the reservoir 25, the product fluid being pressurised by action of the bag 98 which communicates to the product reservoir the pressure provided by hydrocarbon propellant within the propellant fluid reservoir 26. As product fluid is drawn from the product reservoir 25 an imbalance of pressure is created across the bag 98 so that it collapses to a shape having decreased volume until pressure is equalised.

Alternative arrangements in accordance with the present invention are contemplated in which for example any one of the piston arrangements shown in FIGS.

1, 3, 6, 7, 8 and 9 could be incorporated in any of the dispensing apparatus shown in FIGS. 1 and 3. Similarly the container 97 of FIG. 10 could be incorporated in apparatus as described with reference to FIG. 3.

Alternative propellants may be used such as halogenated hydrocarbons for which a compatible elastomeric material is nitrile rubber.

The cap 71 may alternatively include a conical guide for locating the actuator 11, which guide may be a separately moulded part which is a push fit or snap fit on to the gripping formation 72.

The housing 2 may be formed of transparent, translucent or opaque material which may be plain or coloured as required and may be a composite of any combination of such materials formed as a single or multiple stage moulding operation.

What is claimed:

1. Dispensing apparatus for dispensing metered quantities of a pressurized fluid comprising a pressurized dispensing container, a housing for the container defining a bore, the container having a body which is axially slidable in the bore, the container having a collapsible chamber metering valve located at a first end of the body for dispensing metered quantities of fluid and actuated by axial depression of a valve stem defining a dispensing flowpath, a valve actuator fixedly connected to the housing at a corresponding first end there and defining a further dispensing flowpath for product fluid dispensed through the stem, and trigger means operable to urge the container body axially towards the first end of the housing such that the valve stem is depressed by relative movement together of the valve and actuator and thereby dispensing a metered quantity of fluid, wherein the container body defines a chamber and the container includes means dividing the chamber into a product fluid reservoir communicating with the valve and a propellant fluid reservoir, the dividing means being movable such that propellant pressure is applied to the product fluid without mixing of the respective fluids, the dividing means including a free piston axially slidable within the chamber and dividing the chamber into a first portion constituting the product fluid reservoir located forward of the piston and a second portion constituting the propellant fluid reservoir located rearward of the piston, and wherein the piston includes a forward portion of a first material selected to be substantially chemically non-reactive with the product fluid and a rearward portion of a second material selected to be substantially impermeable to the propellant fluid, the piston portions being composited such that the product and propellant fluids respectively do not contact the second and first materials of the piston respectively.

2. Apparatus as claimed in claim 1 wherein the piston portions are formed of resilient materials and each portion includes a respective seal formation resiliently biassed into peripheral sealing contact with the inner wall of the container.

3. Apparatus as claimed in claim 2 wherein the first and second materials are plastics materials and the respective seal formations comprise annular projections formed integrally with the respective portions.

4. Apparatus as claimed in claim 2 wherein the first and second materials are elastomeric, the respective seal formations comprising annular projections of part circular cross-section formed integrally with the respective portions.

5. Apparatus as claimed in claim 1 wherein the piston comprises substantially rigid piston body, first seal means peripherally sealing the piston body to the inner wall of the container and formed of a material selected to be substantially chemically non-reactive with the product fluid and second seal means peripherally sealing the piston to the inner wall of the container at a location rearward of the first seal means and formed of a material selected to be substantially impermeable to the propellant fluid.

6. Apparatus as claimed in claim 5 wherein the first seal means is a ring of bromobutyl rubber material.

7. Apparatus as claimed in claim 5 wherein the second seal means is a ring of nitrile rubber material.

8. Apparatus as claimed in claim 5 wherein the piston body comprises a forward portion, a rearward portion spaced axially and rearwardly of the forward portion and a connecting portion co-operating with the forward and rearward portions to define first and second annular grooves receiving the first and second seal means respectively.

9. Apparatus as claimed in claim 1 wherein the actuator comprises inner and outer nested components, the actuator including a break-up nozzle for atomising dispensed fluid, which nozzle includes swirl inducing ducts defined by groove formations formed in one or other abutting surfaces of the inner and outer nested components of the actuator respectively.

10. Apparatus as claimed in claim 9 in which the inner nested component includes a first tubular portion fitting onto a stem of a co-operating dispensing valve of the container, the outer nested component including a second tubular portion fitting onto the first tubular portion and the first tubular portion being provided with an axially extending groove defining an axially extending dispensing flowpath.

11. Apparatus as claimed in claim 1 wherein the trigger means comprises a trigger member which is pivotally mounted with respect to the housing and further comprising means transmitting pivotal movement of the trigger member to axial movement of the container.

12. Apparatus as claimed in claim 1 wherein the trigger means includes a trigger member which is slidably mounted with respect to the housing and further comprising means transmitting sliding movement of the trigger member to axial movement of the container.

13. Apparatus as claimed in claim 1 wherein the trigger member includes a trigger member which includes at least one projection extending through an aperture of the housing and engaging a co-operating formation of the container, the trigger member being axially slidable and the container being slidable in unison therewith with respect to the housing.

14. Apparatus as claimed in claim 1 wherein the propellant fluid is insulin.

15. Apparatus as claimed in claim 1 wherein the propellant fluid is a hydrocarbon fluid.

16. A pressurized dispensing container having a tubular body defining a chamber, the container having a collapsible chamber metering valve located at a first end of the body for dispensing metered quantities of fluid and actuated by axial depression of a valve stem defining a dispensing flowpath, the container having piston means dividing the chamber into a product fluid reservoir communicating with the valve and a propellant fluid reservoir, the piston means being movable such that propellant pressure is applied to the product fluid without mixing of the respective fluids, the piston means including a free piston axially slidable within the chamber and dividing the chamber into a first portion constituting the product fluid reservoir located forward of the piston and a second portion constituting the propellant fluid reservoir located rearward of the piston, wherein the piston includes a forward portion of a first material selected to be substantially chemically non-reactive with the product fluid and a rearward portion of a second material selected to be substantially impermeable to the propellant fluid, the piston portions being composited such that the product and propellant fluids respectively do not contact the second and first materials of the piston respectively.

17. Dispensing apparatus for dispensing metered quantities of a pressurized fluid comprising a pressurized dispensing container, a housing for the container defining a bore, the container having a body which is axially slidable in the bore, the container having a collapsible chamber metering valve located at a first end of the body for dispensing metered quantities of fluid and actuated by axial depression of a valve stem defining a dispensing flowpath, a valve actuator fixedly connected to the housing at a corresponding first end thereof and defining a further dispensing flowpath for product fluid dispensed through the stem, and trigger means operable to urge the container body axially towards the first end of the housing such that the valve stem is depressed by relative movement together of the valve and actuator and thereby dispensing a metered quantity of fluid, wherein the container body defines a chamber and the container includes a flexible bag dividing the chamber into a product fluid reservoir communicating with the valve and a propellant fluid reservoir, the bag being movable such that propellant pressure is applied to the product fluid without mixing of the respective fluids, and wherein the interior of the bag defines the product reservoir, the bag including a mouth portion including a thickened annular flange secured in sealing contact with a cooperating flange of the valve and a thickened neck portion formed integrally with the flange and depending rigidly therefrom so as to define an annular space between the neck and the valve.

18. Apparatus as claimed in claim 17 wherein the container is secured to the valve by means of a crimped valve ferrule such that the flange comprising the bag mouth is clamped between an annular lip of the container mouth and the valve flange.

19. Dispensing apparatus for dispensing metered quantities of a pressurized fluid comprising a pressurized dispensing container, a housing for the container defining a bore, the container having a body which is axially slidable in the bore, the container having a collapsible chamber metering valve located at a first end of the body for dispensing metered quantities of fluid and actuated by axial depression of a valve stem defining a dispensing flowpath, a valve actuator fixedly connected to the housing at a corresponding first end thereof and defining a further dispensing flowpath for product fluid dispensed through the stem, and trigger means operable to urge the container body axially towards the first end of the housing such that the valve stem is depressed by relative movement together of the valve and actuator and thereby dispensing a metered quantity of fluid, wherein the container body defines a chamber and the container includes means dividing the chamber into a product fluid reservoir communicating with the valve and a propellant fluid reservoir, the dividing means being movable such that propellant pressure is applied to the product fluid without mixing of the respective fluids, and wherein the actuator includes inner and outer nested components, the actuator including a break-up nozzle for atomizing dispensed fluid, which nozzle includes swirl inducing ducts defined by groove formations formed in one or other abutting surfaces of the inner and outer nested components of the actuator respectively, which inner nested component includes a first tubular portion defining a bore fitting onto the valve stem, the outer nested component including a second tubular portion fitting onto the first tubular portion, the first tubular portion being provided with an axially extending groove cooperating with the outer component to define a passageway communicating with the nozzle and a radial port communicating between the bore and the passageway.

20. Dispensing apparatus as claimed in claim 19 wherein the nozzle is of greater diameter than the valve stem.

* * * * *